United States Patent
Garcia et al.

(10) Patent No.: US 9,835,028 B2
(45) Date of Patent: Dec. 5, 2017

(54) DEVICE FOR SAMPLING FLUID UNDER PRESSURE FOR GEOLOGICAL SITE DEVELOPMENT MONITORING

(71) Applicant: IFP Energies nouvelles, Rueil-Malmaison (FR)

(72) Inventors: Bruno Garcia, Rueil Malmaison (FR); Jean Tricard, Paray Vieille Poste (FR); Claudio Fernandes-Marto, Poissy (FR); Virgile Rouchon, Vaucresson (FR); Thierry Walrave, Quartier Saint Vincent (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 545 days.

(21) Appl. No.: 14/492,251

(22) Filed: Sep. 22, 2014

(65) Prior Publication Data
US 2015/0083403 A1 Mar. 26, 2015

(30) Foreign Application Priority Data
Sep. 24, 2013 (FR) ...................................... 13 59196

(51) Int. Cl.
*G01N 1/10* (2006.01)
*E21B 49/08* (2006.01)

(52) U.S. Cl.
CPC ............ *E21B 49/088* (2013.01); *E21B 49/08* (2013.01); *E21B 49/081* (2013.01); *G01N 1/10* (2013.01); *G01N 2001/105* (2013.01); *G01N 2001/1031* (2013.01)

(58) Field of Classification Search
CPC ...... E21B 49/08; E21B 49/081; E21B 49/088; G01N 1/10; G01N 2001/1031; G01N 2001/105
See application file for complete search history.

(56) References Cited

U.S. PATENT DOCUMENTS

| | | | | |
|---|---|---|---|---|
| 2,951,537 A | * | 9/1960 | Desbrandes | E21B 49/10 166/100 |
| 4,270,385 A | * | 6/1981 | Hallmark | E21B 49/10 73/152.26 |
| 5,896,926 A | | 4/1999 | Hama et al. | |
| 5,945,611 A | | 8/1999 | Welker | |

FOREIGN PATENT DOCUMENTS

| | | |
|---|---|---|
| FR | 2972758 A1 | 9/2012 |
| FR | 2974358 A | 10/2012 |

* cited by examiner

*Primary Examiner* — John Fitzgerald
(74) *Attorney, Agent, or Firm* — Fitch, Even, Tabin & Flannery, LLP

(57) ABSTRACT

The invention relates to a fluid sampling device comprising a sample chamber (01) including a lower piston (05), an upper piston (02) and an intermediate piston (28). Intermediate piston (28) is moved so as to guarantee a substantially constant volume for chamber (01) when closing the chamber.

14 Claims, 13 Drawing Sheets

Section A-A

Section B-B

DEVICE FOR SAMPLING FLUID UNDER PRESSURE FOR GEOLOGICAL SITE DEVELOPMENT MONITORING

FIELD OF THE INVENTION

The invention relates to the technical sphere of underground medium development, such as gas reservoir development (gas storage/withdrawal, gas exploitation) and monitoring of these operations (contamination of operations on aquifers). The invention notably relates to the sphere of geological storage site monitoring for gases such as carbon dioxide ($CO_2$) or methane. Other fields such as enhanced oil recovery through $CO_2$ injection for example or exploitation of gas from mother rocks are also concerned by the present invention.

In particular, the invention relates to fluid sampling devices and more particularly to a device for sampling fluids under pressure in a well, a pipeline, a conduit, a line, a reservoir or the like.

Fluids present in wells need to be sampled in order to determine their composition so as to characterize the geological reservoirs reached by the borehole and their evolution over time throughout the industrial storage and/or production process. This is notably the case for geological gas storage site monitoring.

BACKGROUND OF THE INVENTION

Industrialists have developed many techniques allowing the evolution of the fluids injected into porous media to be monitored.

Geochemical monitoring methods for geological $CO_2$ storage sites, based on the study of volatile species, are for example known. Examples of such methods are described in patent applications FR-2,972,758 and FR-2,974,358.

These methods essentially apply for two compartments:

in the reservoir/saline aquifers where the main objective is to quantify the dissolved and precipitated $CO_2$, and thus to establish a real mass balance, in the aquifers overlying the cap rock, where the main objective is to diagnose a leak as early as possible.

To implement these methods, it is thus necessary to have a device for sampling fluids under pressure in a well drilled through a geological formation. Such a device is referred to as sampler.

Samplers referred to as FTS (Flow-Through Sampler), allowing to obtain fluid samples from a well drilled through a geological formation, are known. Such a device is comprised of a sample chamber with a spring-loaded valve at each end. A latching mechanism connects the valves together and holds them open. Above the chamber, there is a clock to program the closing time and a triggering mechanism to release the valves. The lower end is provided with means allowing the fluid to enter. At the top, there is a rope socket for attaching a cable.

U.S. Pat. No. 5,945,611 discloses a device for sampling fluids under pressure in a pipeline, tube, duct, conduit or the like. This device comprises a plurality of pistons, a body having a common passageway, wherein said pistons are slidably mounted, a lateral inlet and a lateral outlet port located within said passageway and communicating with the pipeline, said inlet and outlet ports so arranged that the motion of the pistons can cover and uncover said inlet and outlet ports.

U.S. Pat. No. 5,896,926 discloses a device for in-situ sampling of groundwater under static conditions without disturbing the environment but comprising a packer to isolate the sampling system from the area located above, as well as an in-situ pumping system in said sampler for "sucking" the fluid into the sample chamber.

The French patent application whose application number is FR-12/03,329 (not published yet) discloses a sampling device comprising, on the one hand, a piston controlled by a spring immersed in an oil chamber for sampling the fluid and, on the other hand, a second piston for expelling the fluid upon transfer. The device is kept in open or closed position by the compressed spring housed in the oil-filled chamber. The oil contained in the spring chamber allows the decompression effect to be damped and smooth sampling to be achieved. The device enables recovery of the sampled fluid using the mechanical action of a solid piston through a manual valve. This design allows to avoid mercury systems or piston fluid systems, and to recover all or part of the fluid under controlled pressure conditions. Furthermore, this design allows to avoid using a surge chamber and an oil chamber as in nearly all of the known samplers. Another advantage of this device is that it can be lowered in open position into the underground medium, thus overcoming opening problems and allowing complete filling of the sample chamber. However, the device described in this patent application can pose problems upon closing of the sampler due to the fluid compressibility likely to hinder return of the first piston.

The invention relates to a fluid sampling device comprising a sample chamber including a lower piston, an upper piston and an intermediate piston. The intermediate piston is moved so as to guarantee a substantially constant chamber volume when closing the chamber in order to avoid problems linked with the incompressibility of the sampled fluid.

SUMMARY OF THE INVENTION

The invention relates to a device for sampling at least one fluid under pressure, comprising a sample chamber defining an inner volume intended to receive said fluid. Said device comprises a lower piston arranged in the lower part of said chamber, an upper piston arranged in the upper part of said chamber, an intermediate piston arranged between said lower and upper pistons, means for closing and opening said chamber by moving said lower piston, and means for moving said intermediate piston allowing to define a substantially constant volume for said chamber upon closing of said chamber.

According to one embodiment of the invention, the volume of said chamber is defined by said intermediate piston and said lower piston.

Advantageously, said intermediate piston is arranged at a substantially constant distance from said lower piston in open position and in closed position of said chamber, said intermediate piston resting against said upper piston when said chamber is in closed position.

Furthermore, said device can comprise means for transferring the fluid out of the chamber, said transfer means comprising means for controlling the joint descent of said upper piston and of said intermediate piston from the upper part to the lower part of said chamber.

According to another embodiment of the invention, the volume of said chamber is defined by said intermediate piston and said upper piston.

Advantageously, said intermediate piston is arranged at a substantially constant distance from said upper piston in open position and in closed position of said chamber, said intermediate piston resting against said lower piston in open position and in closed position of said chamber.

Preferably, said upper and lower pistons are connected by a connecting rod on which said intermediate piston slides.

Advantageously, said upper piston is provided with a port allowing circulation of the fluid outside said chamber, and said port can be shut by a needle valve.

Said device can furthermore comprise means for transferring the fluid out of the chamber, said transfer means comprise means for moving said intermediate piston from the lower piston towards the upper piston of said chamber.

According to the invention, the means for opening and closing said chamber comprise a rectilinear element linked to the lower piston and to a spring element so that, in open position, said spring element is compressed.

Advantageously, said lower piston is equipped with a needle valve and a High Pressure connection allowing said fluid to be discharged from said sample chamber.

Besides, the invention relates to a use of the device according to the invention wherein the development of an underground geological site is monitored through fluid sampling in a monitoring well. This method comprises the following stages:

a) actuating said means for closing and opening said chamber of said sampling device so as to bring it into "open" position, b) lowering the device, in "open" position, into the monitoring well, c) holding said device in "open" position in a predetermined position, d) actuating said means for closing and opening said chamber of said sampling device so as to bring it into "closed" position, and e) bringing said device back to the surface.

The following stages can furthermore be carried out:

f) transferring said fluid out of said chamber of the device by actuating fluid transfer means, and g) performing at least one analysis of the sampled fluid.

Preferably, development of an underground geological site consists in monitoring a geological $CO_2$ storage site or monitoring a natural gas storage/withdrawal site or monitoring a shale gas development site or monitoring enhanced oil recovery sites using gas injection, notably $CO_2$.

BRIEF DESCRIPTION OF THE FIGURES

Other features and advantages of the method according to the invention will be clear from reading the description hereafter of embodiments given by way of non limitative example, with reference to the accompanying figures wherein.

DETAILED DESCRIPTION

The device for sampling fluids under pressure according to the invention is based on the principle of samplers known as FTS (Flow-Through Sampler) wherein the liquid from the well freely circulates within the device.

Figure 1:
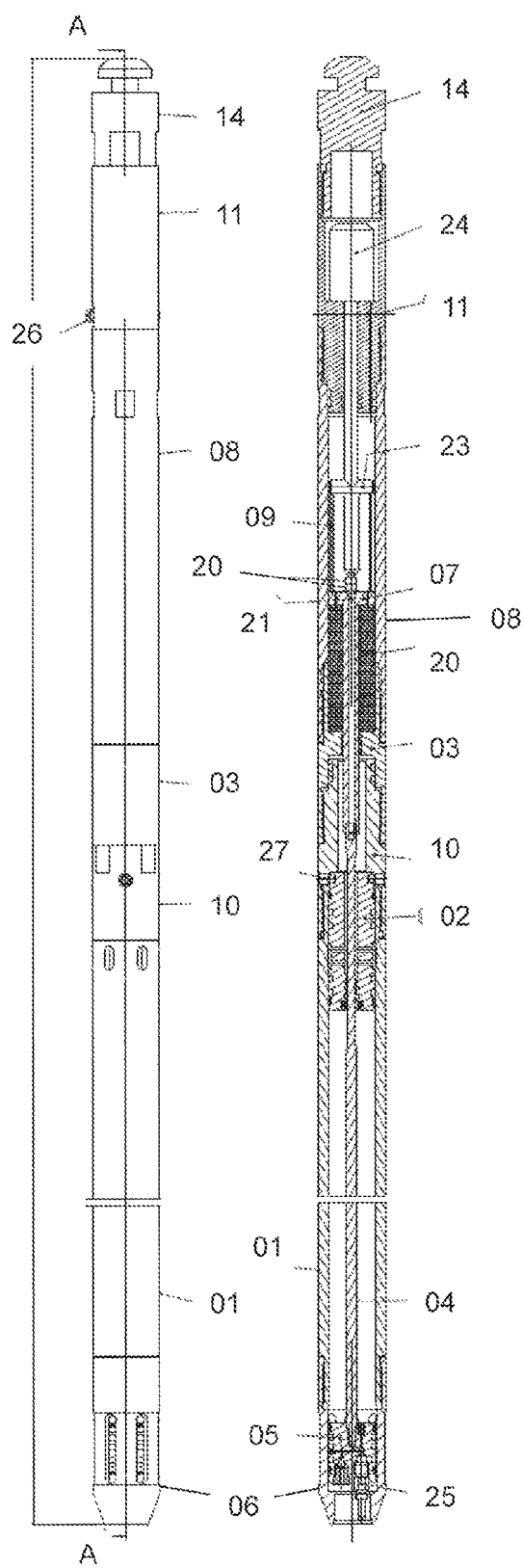
FIG. 1 illustrates the device according to the prior art (FR-12/03,329) in "open" position. The figure at the right is a cross-section along axis A-A of the figure at the left.
Figure 2:
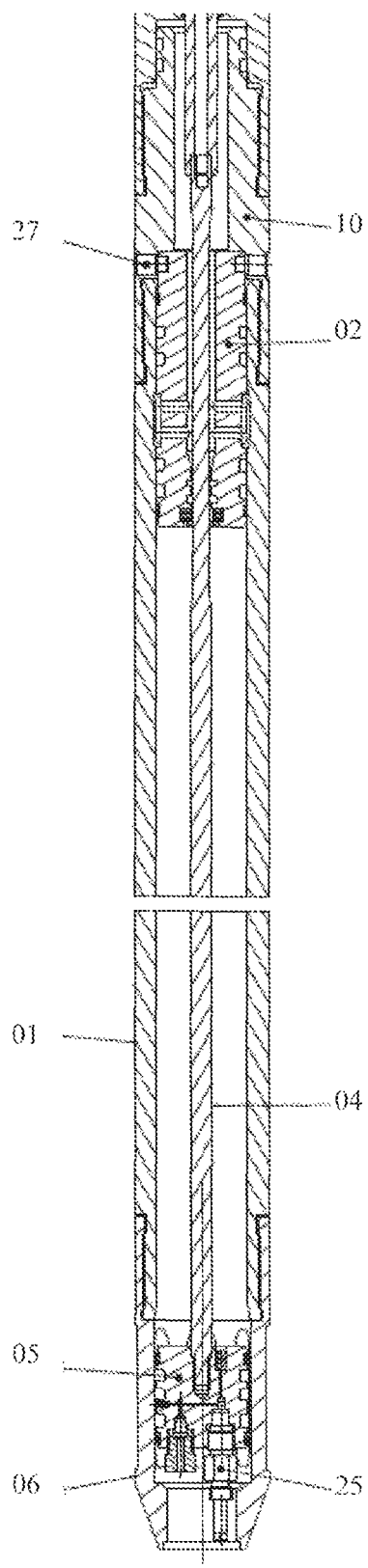
FIG. 2 shows the lower part of the device according to the prior art (FR-12/03,329)
Figure 3:
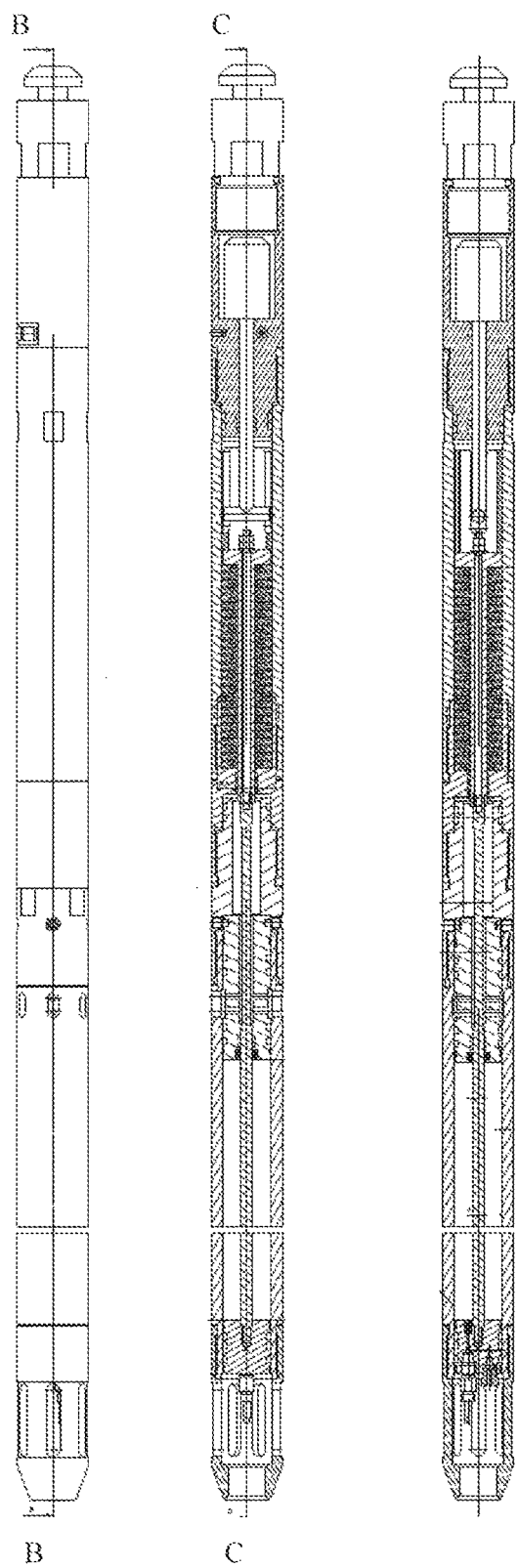
FIG. 3 illustrates the device according to the prior art (FR-12/03,329) in "closed" position. The figure in the middle is a cross-section along axis B-B of the figure at the left, and the figure at the right is a cross-section along axis C-C of the figure in the middle.

FIGS. 1 to 3 illustrate the device according to the prior art (as described in French patent application with application number FR-12/03,329) for sampling fluids under pressure. In these figures, the same reference numbers have been used. The device comprises at least:
a sample chamber (01),
a body (10, 03, 08) surmounting said sample chamber,
circulation means for circulating the fluid in said chamber,
holding means for holding the fluid in said chamber, and
transfer means for transferring the fluid out of said chamber.

For the sampler according to this prior art, the holding means comprise a lower piston (05) suited to allow or prevent passage of the fluid into the lower part of said chamber (01), said lower piston (05) being moved by means including an elastic element (20) arranged in an oil-filled chamber within said body and connected to said piston by a rectilinear element (04) such as a rod (04) for example.

The transfer means comprise means for controlling the descent of an upper piston (02) from the upper part to the lower part of said chamber, so that said fluid remains at constant pressure in said chamber (01).

FIG. 1 illustrates the device of the prior art in "open" position. The figure at the right is a cross-section along axis A-A of the figure at the left. FIG. 2 shows the lower part of the device according to the prior art. FIG. 3 illustrates the device according to the prior art in "closed" position. The figure in the middle is a cross-section along axis B-B of the figure at the left, and the figure at the right is a cross-section along axis C-C of the figure in the middle. Thus, the device according to the prior art comprises (FIG. 1) a sample chamber (01). The purpose of this chamber is to receive the fluid under pressure (under downhole conditions). The sample chamber can comprise a shell (01) defining an inner volume to receive the fluid. The lower part of chamber (01) can be screwed onto a lower end piece (06) comprising at least one port allowing passage of the fluid. The upper part of chamber (01) is screwed onto a body (10, 03, 08). The chamber also comprises a port in the upper part thereof so as to circulate the fluid within chamber (01): the fluids flows in through the lower port of the chamber or through the port of lower end piece (06) and it flows out through the port of chamber (01) in the upper part thereof.

The body comprises a chamber filled with oil in which an elastic element (20) is immersed. This elastic element can be a spring or a set of Belleville washers. It can be connected to lower piston (05) by a brace (07) and a rod (04).

This lower piston (05) is suited to allow or to prevent passage of the fluid under pressure into the lower part of chamber (01). Thus, in high position, piston (05) is positioned at least partly in chamber (01), at the lower end thereof, sealingly closing the inlet thereof (the piston is provided with joints for example). In low position, the piston moves out of chamber (01), thus allowing the fluid to flow in. When chamber (01) is provided with a lower end piece (06), this end piece (06) has a length allowing lower piston (05) to move out of the chamber and thus allowing passage of a fluid into sample chamber (01) via the port.

Thus, when elastic element (20) is compressed (FIGS. 1 and 2), rod (04) drives (assisted by brace (07)) lower piston (05) out of sample chamber (01) so as to allow passage of a fluid into the chamber. On the other hand, when elastic element (20) is relaxed (FIGS. 3 and 4), rod (04) drives lower piston (05) upwards so as to sealingly close sample chamber (01) in the lower part thereof.

As illustrated in FIGS. 1 and 2, lower piston (05) can be equipped with a needle valve (25) and a high-pressure connection allowing the fluid to be discharged out of sample chamber (01) when the device has been brought back to the surface and the fluid sample is to be analyzed.

A second piston (02) referred to as upper piston is positioned in chamber (01), at the upper end thereof when the fluid is not transferred out of the chamber. This upper piston (02) is suited to slide in the chamber from one end to the other. It has a central port allowing an upper part of rod (04) to slide and providing a seal with a lower part of rod (04), the diameter of the lower port of rod (04) being larger than that of the upper part. Thus, when elastic element (20) is relaxed, rod (04) cooperates with upper piston (02) so as to sealingly close said sample chamber (01) in the upper part thereof. Rod (04) is therefore provided with a shoulder that plugs the hole of upper piston (02). This upper piston (02) can be locked by suitable locking screws (27).

The chamber can be closed in the upper part thereof by an element of body (10, 03, 08) referred to as connector tube (10). This connector tube is fastened to an upper tube (08) through the agency of another tube (03).

Operation of the Device According to the Prior Art

Device in "open" position (FIGS. 1, 2)

In open position, the fluid under pressure circulates freely within sample chamber (01). In this position, spring (20) is tightened and kept at a certain compression level (80% for example) by a handle (23) connected to the shaft of the motor (or of the clock).

In this configuration, lower piston (05) is in low position. The well fluid thus circulates freely through the sample chamber (while the sampler is being lowered into the well for example). In the lower part of the chamber, the fluids flows through the ports of end piece (06), then it flows upward in the chamber and between rod (04) and upper piston (02). A series of bores and openings allows the fluid to circulate through the ports (oblong openings) of shell (01).

According to an embodiment, the ports (oblong openings) of chamber (01) and of end piece (06) are equipped with a grid (80-µm mesh size for example) for screening the solid particles of the fluid.

Device in "closed" position: the sample chamber is locked (FIG. 3)

To start sampling, spring (20) is released. A handle (23) can therefore be rotated and, after achieving a quarter turn, it faces the opening of shell (09). Spring (20) is then released and relaxes, thus driving along: brace (07), rod (04) and lower piston (04). Since the spring chamber is filled with oil, this upward motion occurs smoothly and does not disturb the sampled fluid.

Once the spring relaxed, piston (05) is in the lower part of shell (01) and sealing is provided in the lower part of the sample chamber. In the upper part, sealing is provided by rod (04) on upper piston (02) through the larger diameter at the base of the rod. The fluid sample is isolated and sealed. The sampler can be taken up to the surface.

To turn handle (23), two embodiments are described:

a surface operator actuates electric motor (24) at the appropriate time. This motor rotates handle (23), an on-board stand-alone clock actuates handle (23) at the programmed date and time.

Device in "Transfer" Position

Figure 14:
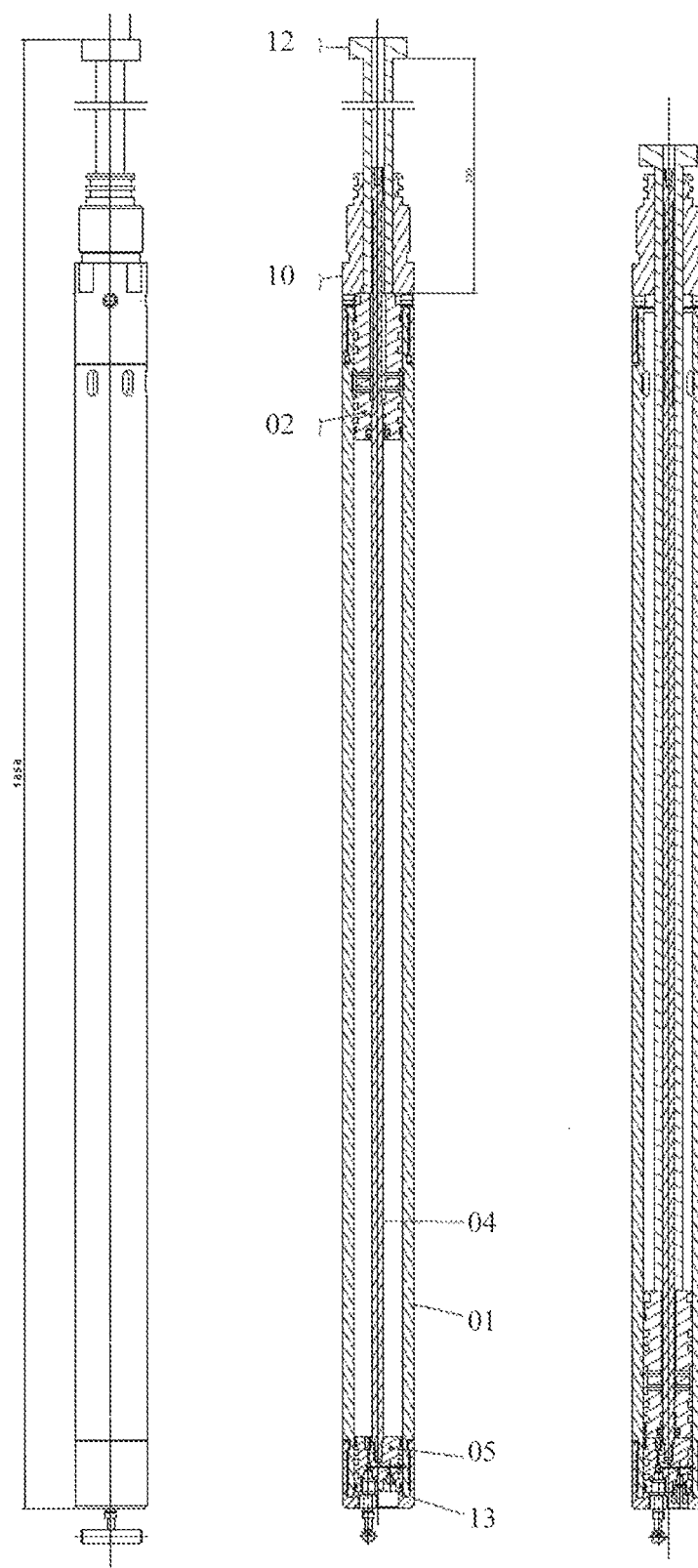
FIG. 14 illustrates the position of the device according to the prior art in "transfer" position. The figure in the middle is a cross-section along axis A-A of the figure at the left with the fluid-filled chamber and the figure at the right is a cross-section along axis A-A of the figure at the left with the empty chamber.
Figure 15:
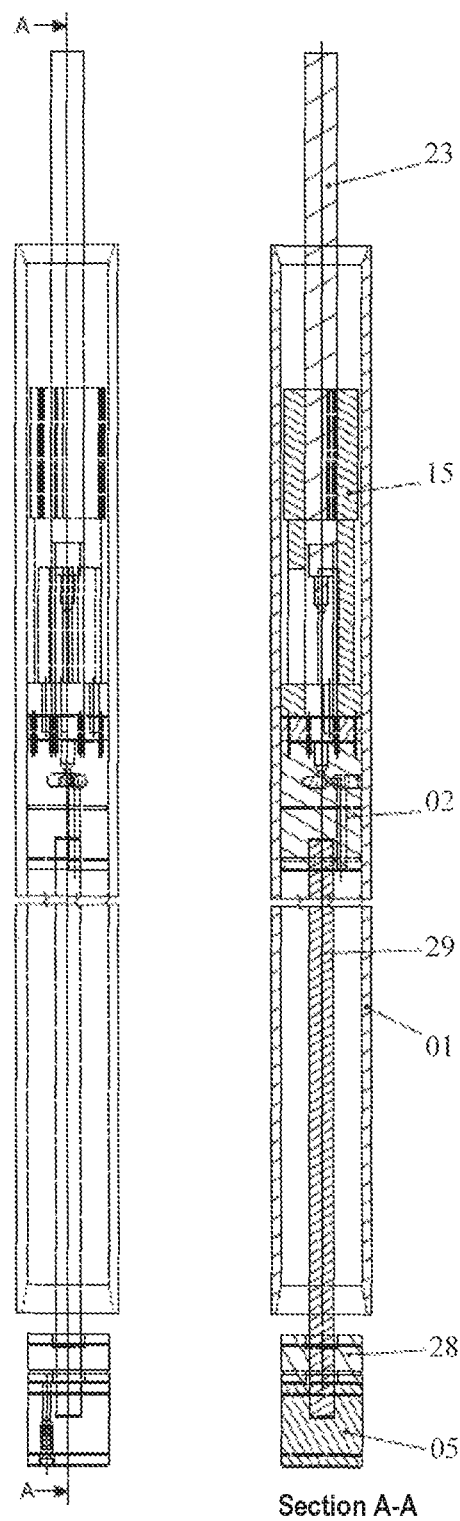
FIG. 15 illustrates a device according to the second embodiment of the invention in "open" position. The figure at the right is a cross-section along axis A-A of the figure at the left.
Figure 16:
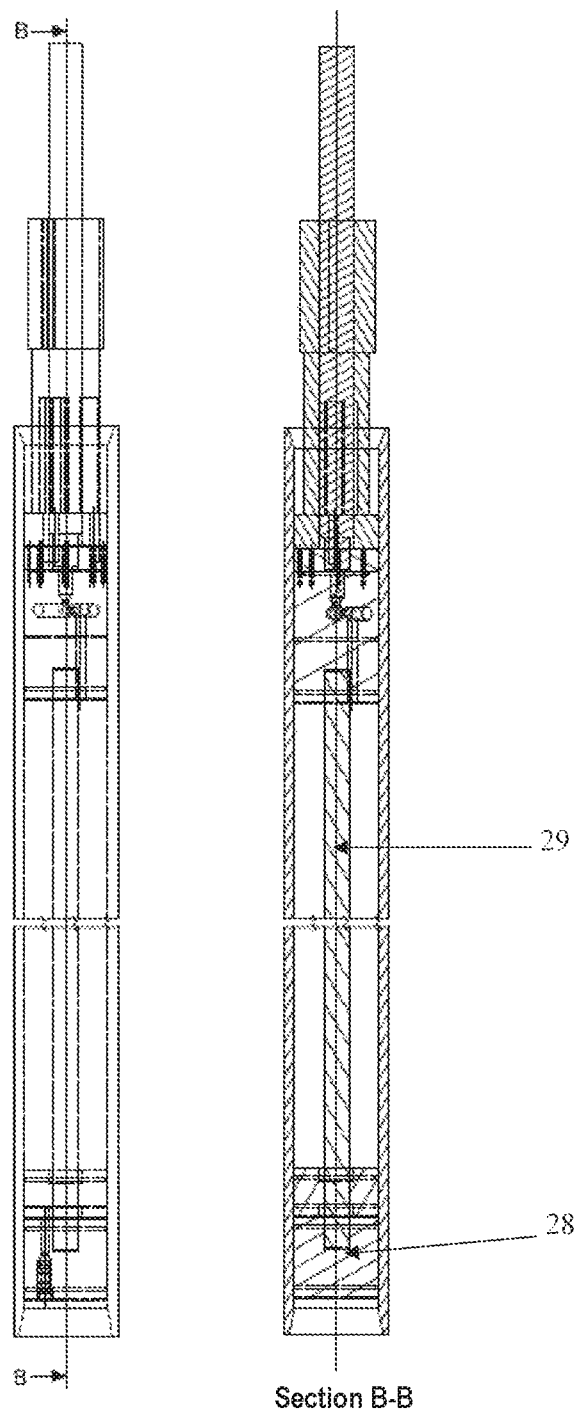
FIG. 16 illustrates a device according to the second embodiment of the invention in "closed" position. The figure at the right is a cross-section along axis B-B of the figure at the left.

FIG. 14 illustrates the position of the device in "transfer" mode. The figure in the middle is a cross-section along axis A-A of the figure at the left with the chamber filled with fluid, and the figure at the right is a cross-section along axis A-A of the figure at the left with the chamber emptied. Once the device has been raised to the surface, the fluid sample can be transferred. It is thus possible to:

unscrew end piece (06) and replace it by an end piece (13) allowing lower piston (05) to be locked in position within chamber (01), drain the oil from the spring chamber via needle valve (25) and collect the oil by connecting to the HP connection, remove the "motor and hooking" part by unscrewing connector tube (11), unscrew tube (8), remove nuts (22) and unscrew bolt (21), unscrew connector tube (03), then remove it with support brace (07) and spring (20), engage a transfer piston (12) until it rests against upper piston (02), unscrew lock screws (27), connect to the HP connection of lower piston (05), apply the transfer motion of piston (12) to upper piston

(02) and open needle valve (25), and transfer is completed once upper piston (02) rests on lower piston (05).

The sampler according to the invention is an improvement upon the sampling device described above in reference to FIGS. 1 to 3.

Thus, the device according to the invention comprises at least:
- a sample chamber (01),
- a body (10, 03, 08) surmounting said sample chamber,
- circulation means for circulating the fluid in said chamber,
- holding means for holding the fluid in said chamber, and
- transfer means for transferring the fluid out of said chamber.

The sampler according to the invention differs from the device according to the prior art in that it uses a third piston, referred to as intermediate piston, arranged between the lower and upper pistons. The purpose of the intermediate piston is to keep a substantially constant chamber volume while the fluid flows into and remains in the chamber, i.e. when the chamber is closed by the lower piston. The intermediate piston is therefore kept at a substantially constant distance from one of the other two pistons (lower and upper) so as to delimit the volume of the chamber. It is reminded that a piston is a rigid or articulated mechanical part moving in a chamber to provide the volume variation of the chamber; a piston allows a pressure to be converted to mechanical energy and conversely.

The sampler according to the invention furthermore comprises means for closing and opening the chamber by moving the lower piston, and means for moving the intermediate piston allowing to define a substantially constant chamber volume when the chamber is closed.

The device according to the invention can also comprise the other characteristics of the sampler according to the prior art, for example: the means for closing and opening said chamber that move the lower piston, the means for relaxing or compressing the elastic element, the liquid circulation ports (end piece), etc.

According to a first embodiment of the invention, the volume of the chamber is defined by the intermediate piston and the lower piston, i.e. the intermediate piston is at a substantially constant distance from the lower piston. The intermediate piston moves together with the lower piston when the fluid is being sampled ("open" position) and held in place ("closed" position), and it moves together with the upper piston during fluid transfer. Thus, during sampling ("open" position), a variable-volume mini-chamber is formed upon sampling between the intermediate piston and the upper piston, and a sample chamber of substantially constant volume is formed between the intermediate piston and the lower piston.

Figure 4:
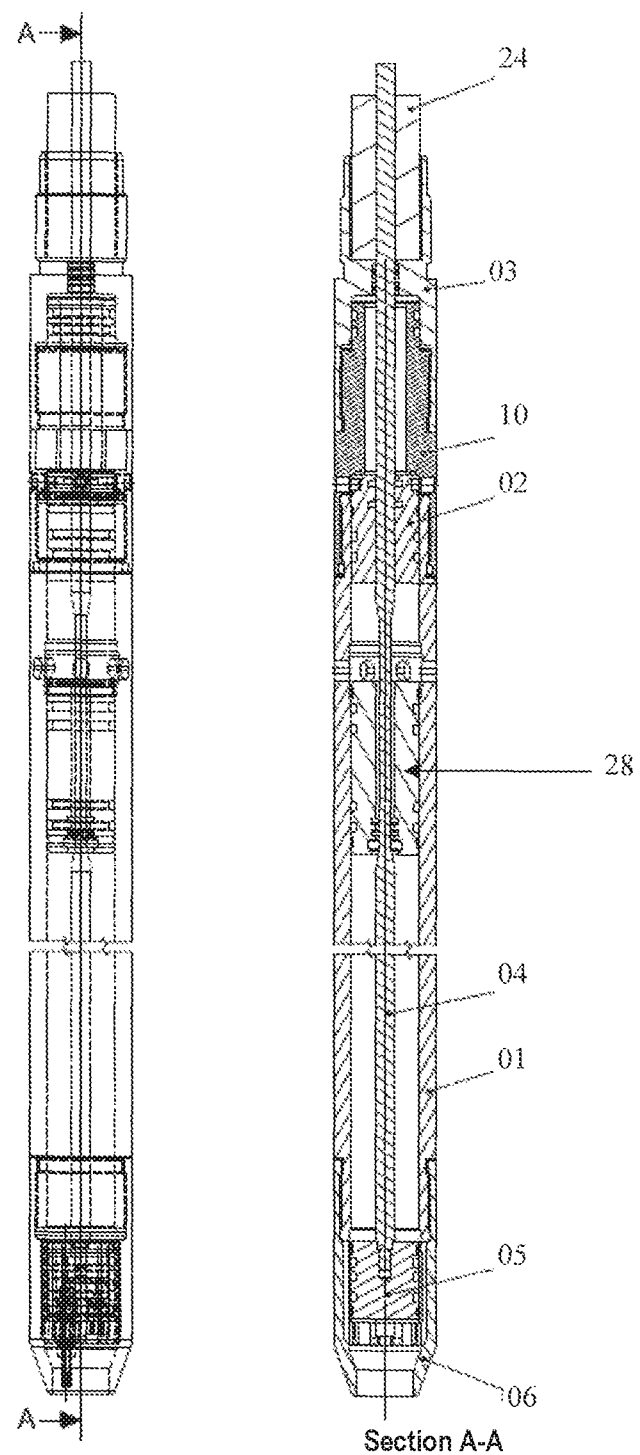
FIG. 4 illustrates a device according to a first embodiment of the invention in "open" position. The figure at the right is a cross-section along axis A-A of the figure at the left.
Figure 5:
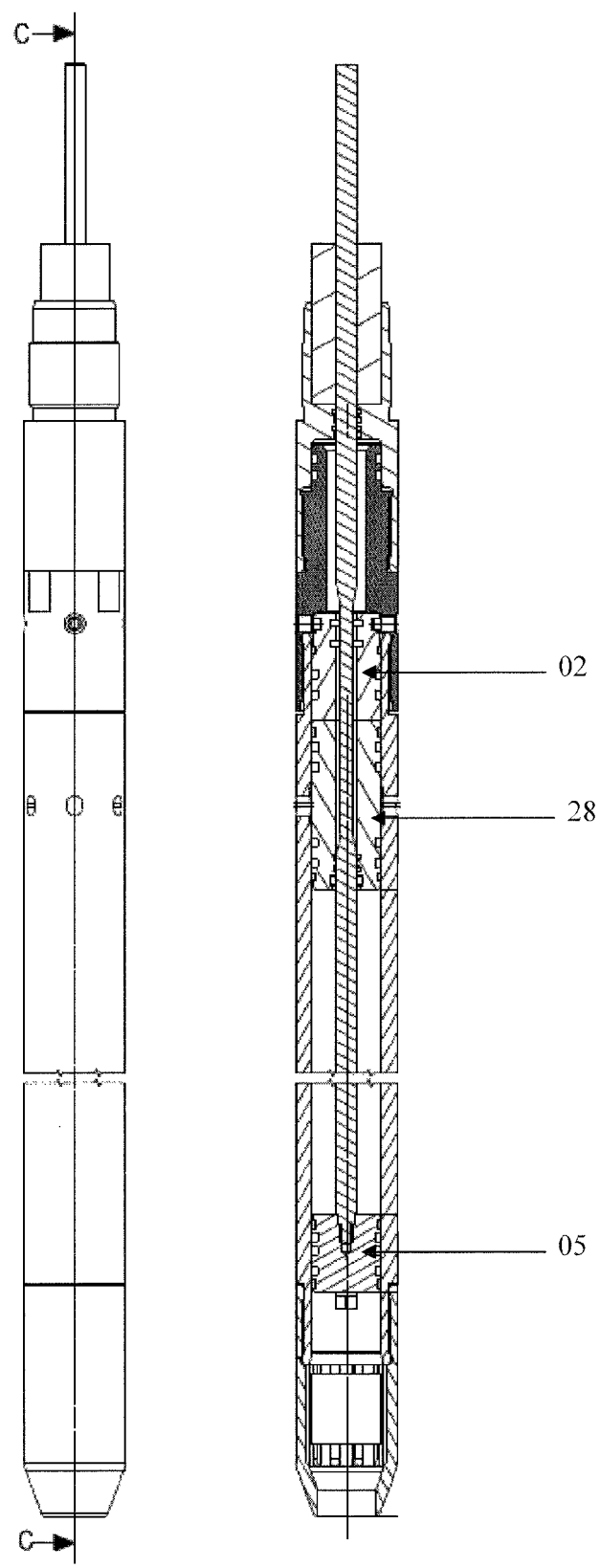
FIG. 5 illustrates the device according to the first embodiment of the invention in "closed" position. The figure at the right is a cross-section along axis C-C of the figure at the left.
Figure 6:
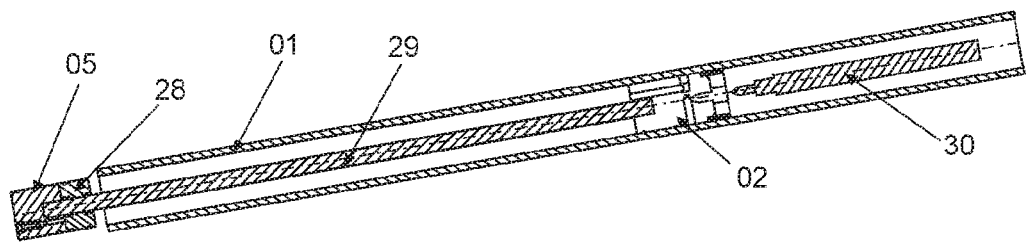
FIG. 6 illustrates a chamber of a device according to a second embodiment of the invention in "open" position.
Figure 7:
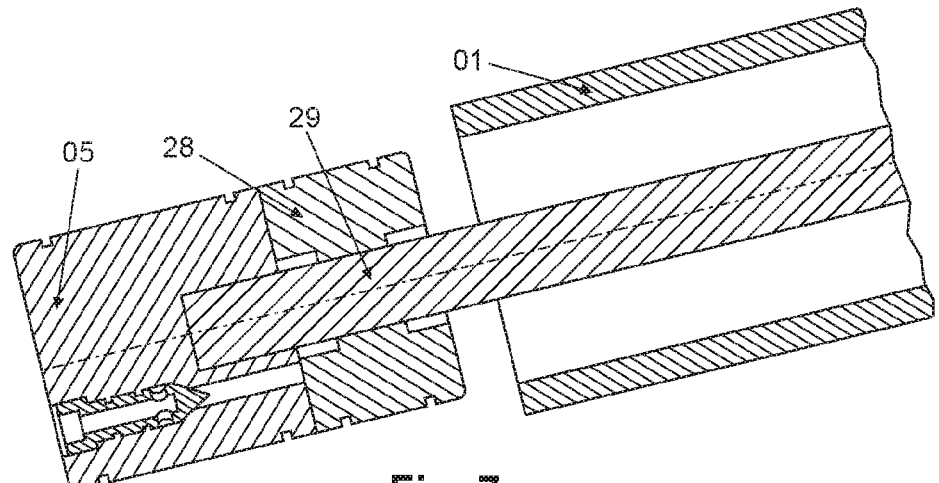
FIG. 7 is a detail view of the lower part of the chamber of the device according to the second embodiment of the invention in "open" position.
Figure 8:
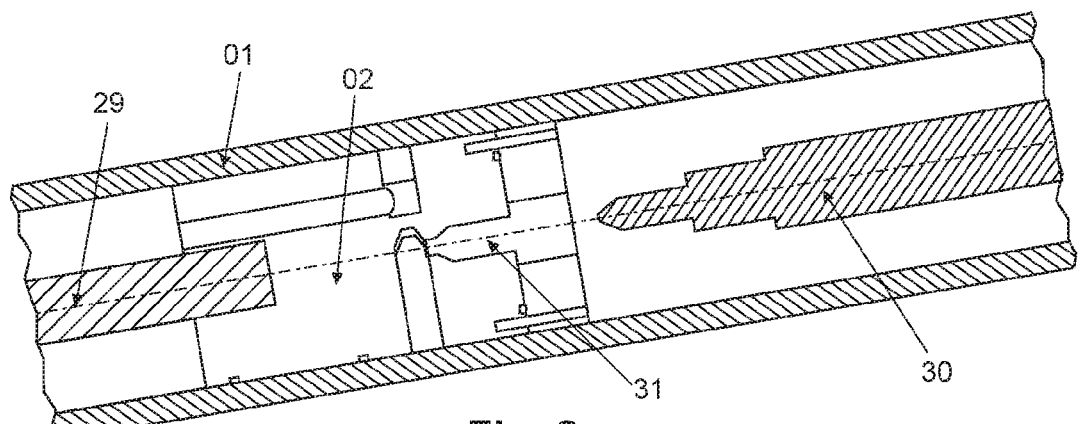
FIG. 8 is a detail view of the upper part of the chamber of the device according to the second embodiment of the invention in "open" position.
Figure 9:
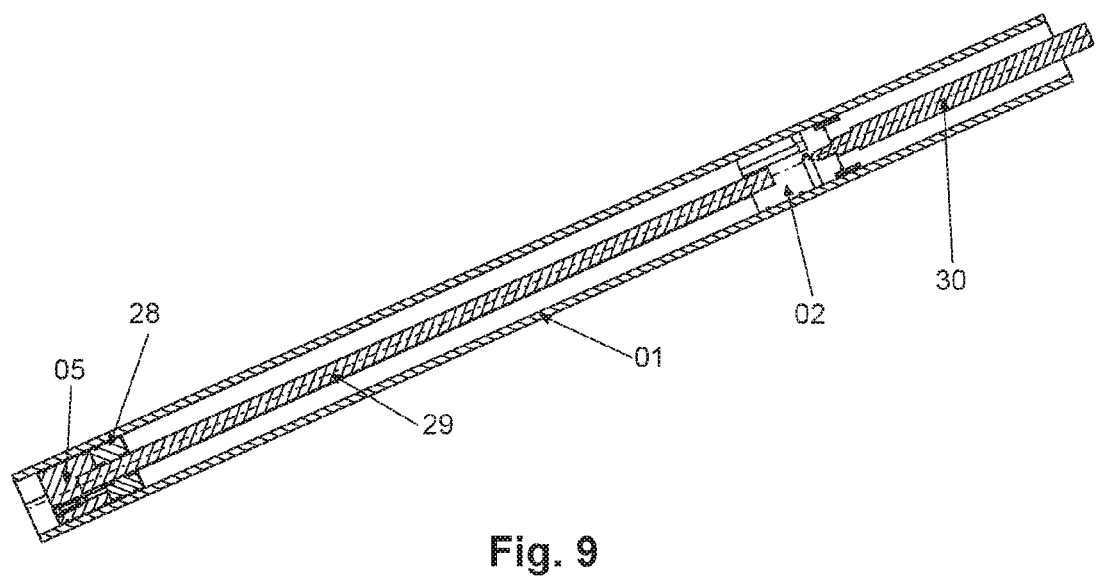
FIG. 9 illustrates a chamber of the device according to the second embodiment of the invention in "closed" position.
Figure 10:
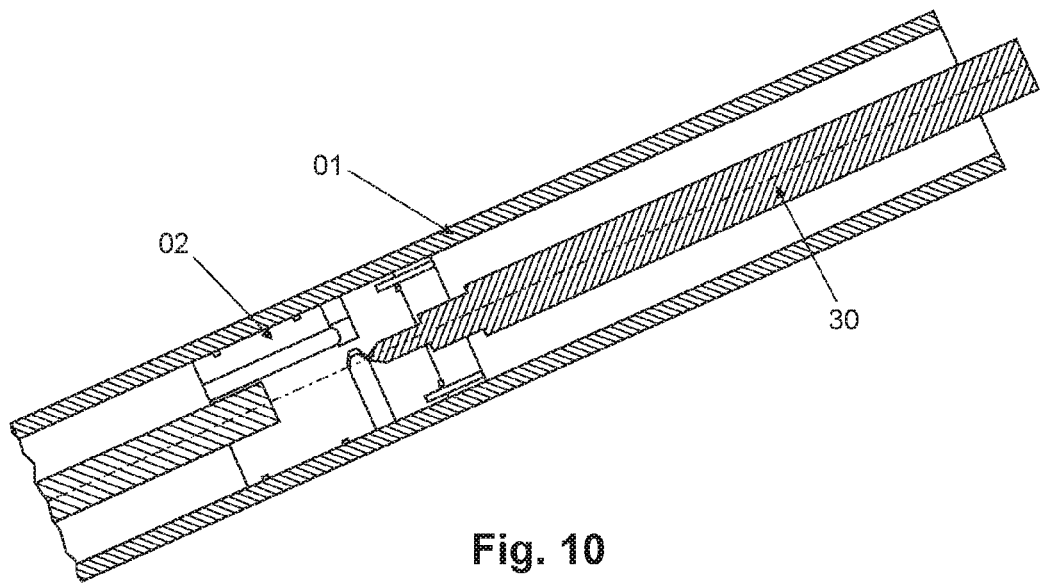
FIG. 10 is a detail view of the upper part of the chamber of the device according to the second embodiment of the invention in "closed" position.
Figure 11:
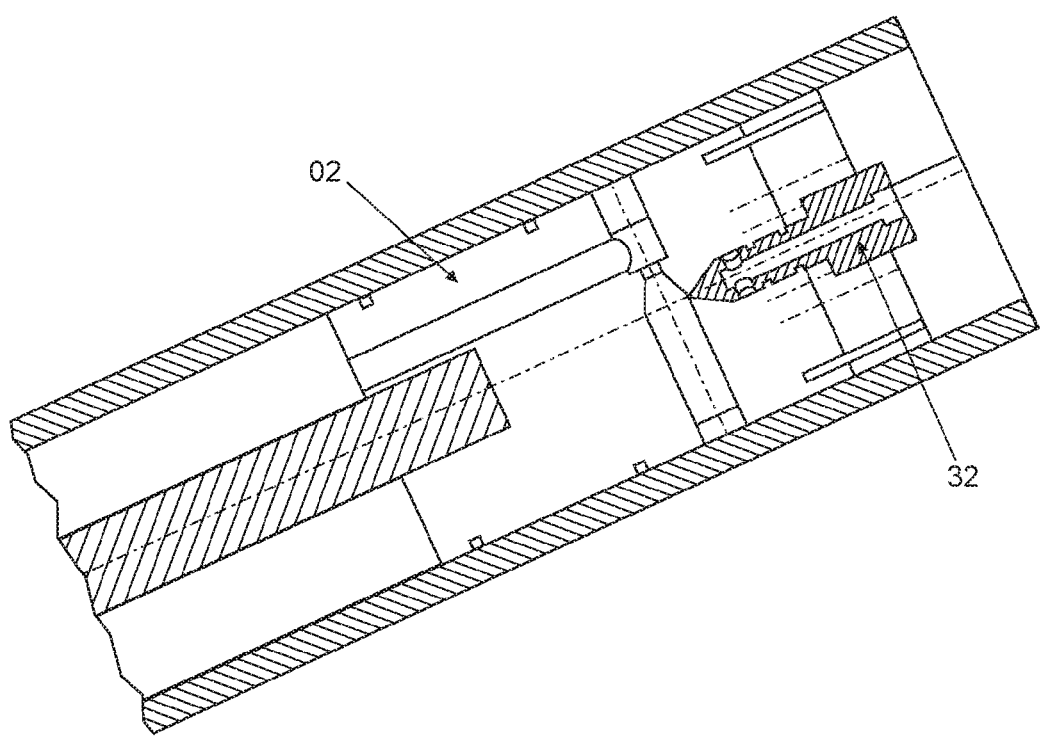
FIG. 11 is a detail view of the upper part of the chamber of the device according to the second embodiment of the invention in "transfer" position.

FIGS. 4 and 5 illustrate this first embodiment in "open" and "closed" position respectively. In these figures, the reference numbers used are identical to those used in FIGS. 1 to 3. Intermediate piston (28) can slide on rod (04).

In "open" position, intermediate piston (28) is lowered and at a distance from upper piston (02), lower piston (05) is lowered in end piece (06) so as to allow passage of the fluid and upper piston (02) is in high position. The fluid flows in through the lower part of the filling chamber, part of the fluid can circulate towards the variable-volume mini-chamber through intermediate piston (28), notably at the center thereof through which rod (04) passes and it can flow out of the sampler through bores in shell (09).

In "closed" position, intermediate piston (28) is moved towards upper piston (02) and comes to an end position against upper piston (02), both in high position, lower piston (05) has moved back up and prevents passage of the fluid. Between the "open" and the "closed" positions, the displacements of the lower (05) and intermediate (28) pistons are substantially identical while keeping a substantially constant spacing distance.

For fluid transfer, according to a first embodiment, the upper (02) and intermediate (28) pistons descend together from the upper part of chamber (01) to the lower part of chamber (01) so that the fluid remains at constant pressure in the chamber during transfer. According to a second embodiment, only intermediate piston (28) descends from the upper part of chamber (01) to the lower part of chamber (01).

Sliding of intermediate piston (28) occurs through the compressibility of the fluid that is sampled in the lower part of chamber (01) and comes to an "end position" at the rod-intermediate joint junction. Intermediate piston (28) moves until it reaches upper piston (02). The distance traveled is equivalent to the distance required for closing the sampler, i.e. for lower piston (05) to go beyond the fluid circulation systems in the lower part until perfect sealing is obtained.

According to a second embodiment of the invention, the volume of the chamber is defined by the intermediate piston and the upper piston, i.e. the distance between the intermediate piston and the upper piston is substantially constant. The intermediate piston moves together with the upper piston when the fluid is being sampled ("open" position) and held in place ("closed" position), and it moves during fluid transfer. Thus, when the fluid is sampled and held in place, a sample chamber of substantially constant volume is formed upon sampling between the intermediate piston and the upper piston.

FIGS. 6 to 11, 15 and 16 illustrate this second embodiment in "open" position, in "closed" position and in "transfer" position. In these figures, the reference numbers used are identical to those used in FIGS. 1 to 5.

Chamber (01) comprises two pistons (02, 05) connected by a connecting rod (29) that can slide in chamber (01) and an intermediate piston (28) sliding on connecting rod (29). Motion of the mobile assembly (lower (05) and upper (02) pistons and connecting rod (29)) in chamber (01) can be provided by a threaded shaft provided with a needle valve (30) at one end. This shaft (30) can be driven by an electric motor. Upper piston (02) is provided with an opening (31) allowing circulation of the fluid in chamber (01). The purpose of needle valve (30) is to close the chamber once sampling is completed by plugging opening (31) of the upper piston.

Prior to sampling ("open" position), intermediate piston (28) is secured to lower piston (05) by creating a negative pressure between these pistons. The assembly made up of the pistons and the connecting rod (02, 05, 28, 29) is brought into low position so that lower piston (05) and intermediate piston (28) are out of the tube, thus opening the lower part of chamber (01) and allowing the fluid to flow in, and the opening of upper piston (02) is disengaged from shutoff valve (30), which allows circulation of the fluid in the chamber.

During displacement of the sampler (in "open" position) down to the sampling depth (FIGS. 6 to 8 and 15), the fluid flowing in through the lower part of chamber (01) circulates in chamber (01) and flows out through opening (31) provided therefore in upper piston (02), then it is discharged through ports arranged in the upper part of chamber (01).

During sampling, in "closed" position (FIGS. 9, 10 and 16), mobile assembly (02, 28, 05, 29) is brought back into chamber (01), which has the effect of closing the lower part of chamber (01), of closing opening (31) of upper piston (02) with the needle valve located at the end of threaded shaft (30) allowing displacement, and of trapping the fluid to be analyzed in a sealed constant-volume chamber (01).

Once the sampler pulled up to the surface (FIG. 12), closing a secondary shutoff valve allows to remove shaft (30) allowing translation with its needle valve and to screw on a transfer valve (32) instead. In closed position, the needle valve seals the chamber. The secondary shutoff valve can then be open. After connecting the analysis circuit to the central valve conduit, the valve just needs to be loosened to open chamber (01) and allow the content thereof to flow out through the conduit. The entire content of chamber (01) can be transferred by increasing the pressure between lower piston (05) and intermediate piston (28) through the agency of a valve, which has the effect of driving intermediate piston (28) towards upper piston (02) and to empty the chamber.

Figure 12:
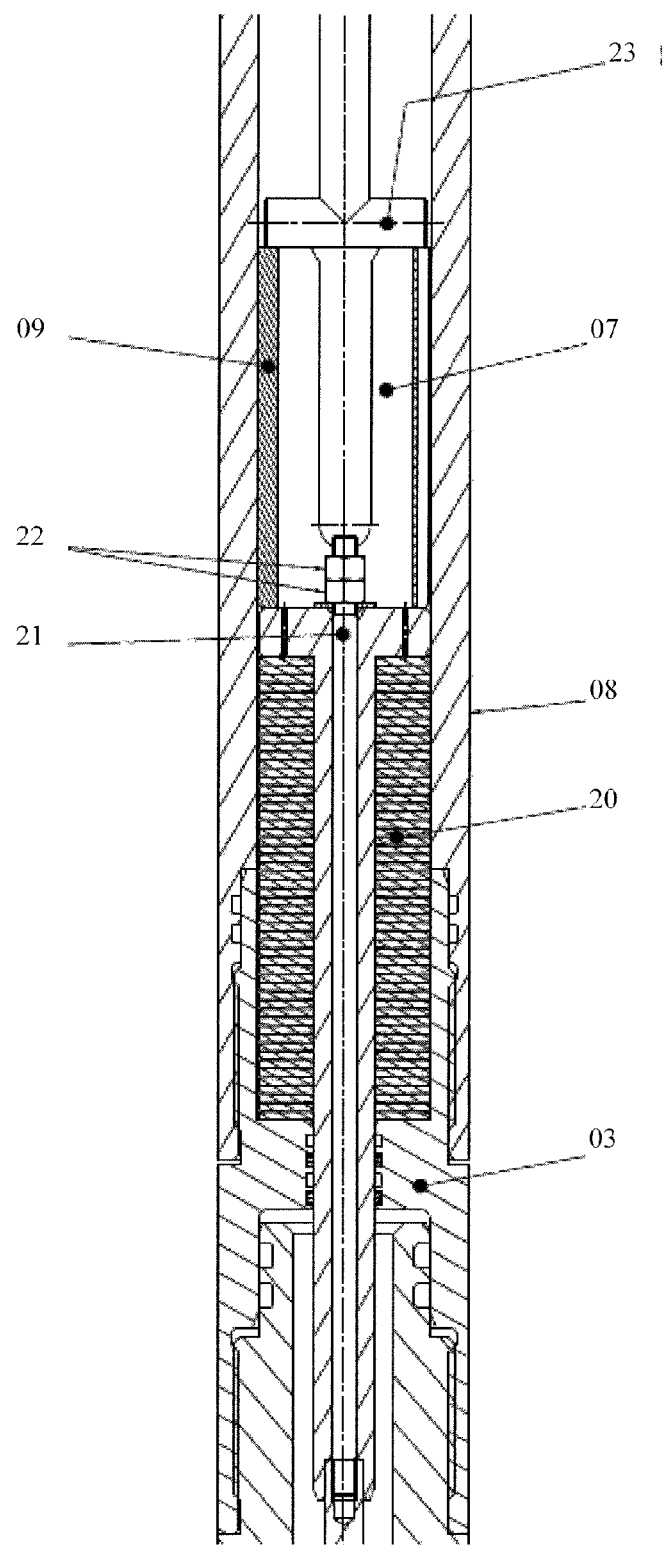
FIG. 12 shows the central part of the device according to the invention.

FIG. 12 shows the central part of the device according to the invention. Upper tube (08) comprises spring element (20) and means (07, 22, 09, 23) for relaxing or compressing it. These means allowing displacement of at least lower piston (05) can comprise:

a support brace (07) for the spring with a bolt (21) and nuts (22), a split collet (09) that releases or locks the spring in compression, and a handle (23) that holds the spring compressed.

Figure 13:
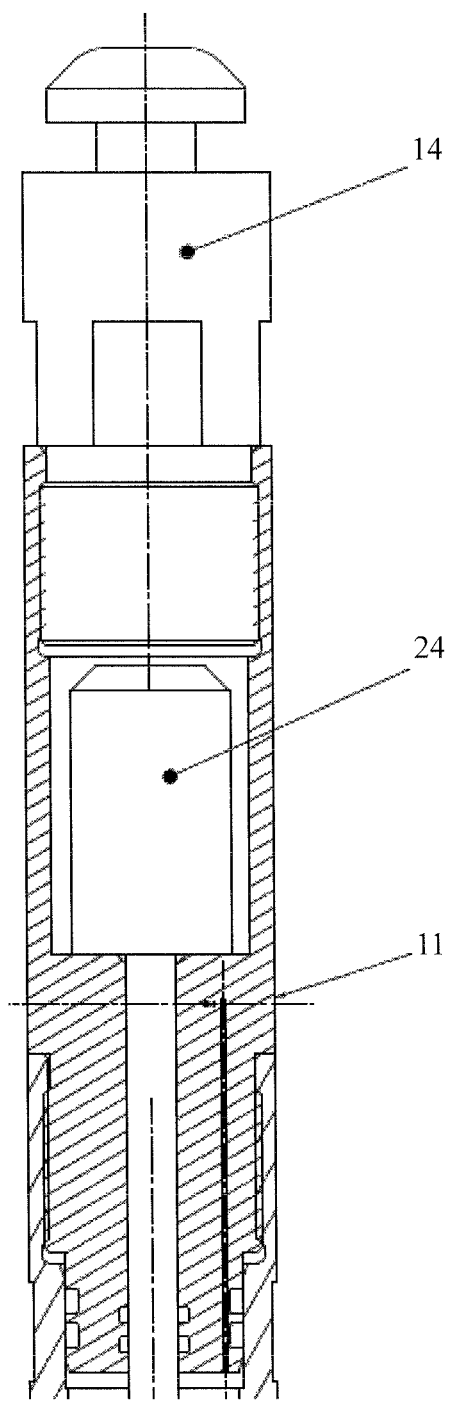
FIG. 13 shows the upper part of the device according to the invention.

FIG. 13 shows the upper part of the device. Means (07, 22, 09, 23) for relaxing or compressing said spring element (20) can be connected to an electric motor controlled on the surface or a programmable clock (24). This motor part is arranged in a housing tube (11) fastened to body (10, 03, 08), at the level of upper tube (08). This motor part is surmounted by a latching part (14) allowing the device to be fastened to a cable and lowered into a well.

The motor or clock (24) cooperates with handle (23) by means of a shaft.

Besides, housing tube (11) is provided with a needle valve (26) and a High Pressure connection for filling the spring chamber with oil.

Another advantage of this device is that it can be lowered in open position into the underground medium, thus overcoming opening problems within the underground medium and allowing complete filling of the sample chamber.

Use of the Device

The invention also relates to a method of monitoring the development of an underground geological site. It can concern:

monitoring a geological $CO_2$ storage site monitoring a natural gas storage/withdrawal site monitoring an enhanced oil recovery site through gas injection, notably $CO_2$, or monitoring a shale gas development site.

Using the device according to the invention for monitoring the development of an underground geological site by sampling fluid under pressure by means of a monitoring well then comprises the following stages:

actuating the means for circulating the sampling device so as to bring it into "open" position, for example by actuating the handle so as to compress the elastic element, lowering the device, in "open" position, into the monitoring well, for example by means of a cable fastened to the upper part of the device, holding the sampling device in "open" position at a predetermined depth, for a predetermined time, actuating the means for holding the device so as to bring it into "closed" position, for example by actuating the handle so as to release the elastic element, bringing the device back to the surface using a cable for example, transferring the fluid out of the chamber of the device by actuating the transfer means, for example by pushing the upper piston while controlling the pressure by means of a pressure detector, so that the pressure in the chamber remains constant, and performing analyses of the sampled fluid, such as: analysis of the cationic and anionic aqueous species, analysis of the so-called trace elements, analysis of the dissolved organic and inorganic carbon, analysis of the dissolved gases (main and rare gases).

All the analyses are interpreted and allow notably to determine whether a $CO_2$ leak is present on the storage site and, if so, which type of leak.

To turn the handle, there are two possible modes:

a surface operator actuates electric motor (24) at the appropriate time. This motor rotates handle (23), or an on-board stand-alone clock actuates handle (23) at the programmed date and time.

The device according to the invention can also be used for sampling fluids under pressure in a pipeline, a tube, a duct, a reservoir or the like in order to analyze these fluids.

The invention claimed is:

1. A device for sampling at least one fluid under pressure, comprising a sample chamber defining an inner volume intended to receive said fluid, a lower piston arranged in the lower part of said chamber, an upper piston arranged in the upper part of said chamber, and an intermediate piston arranged between said lower and upper pistons, wherein said lower piston is configured to move between a closed position closing said chamber and an open position opening said chamber, and said intermediate piston configured to move to define a substantially constant volume for said chamber upon moving of said lower piston to the closed position for closing of said chamber.

2. A device as claimed in claim 1, further comprising a rectilinear element linked to the lower piston and to a spring element to open and close said chamber so that, in the open position, said spring element is compressed.

3. A device as claimed in claim 1, wherein said lower piston is equipped with a needle valve and a High Pressure connection allowing said fluid to be discharged from said sample chamber.

4. A device as claimed in claim 1, wherein the volume of said chamber is defined by said intermediate piston and said lower piston.

5. A device as claimed in claim 4, wherein said intermediate piston is arranged at a substantially constant distance from said lower piston in open position and in closed position of said chamber, said intermediate piston resting against said upper piston when said chamber is in closed position.

6. A device as claimed in claim 4, wherein said upper piston and said intermediate piston are configured to jointly descend from the upper part to the lower part of said chamber to transfer fluid out of the chamber.

7. A device as claimed in claim 1, wherein the volume of said chamber is defined by said intermediate piston and said upper piston.

8. A device as claimed in claim 7, wherein said intermediate piston is arranged at a substantially constant distance from said upper piston in open position and in closed position of said chamber, said intermediate piston resting against said lower piston in open position and in closed position of said chamber.

9. A device as claimed in claim 7, wherein said upper and lower pistons are connected by a connecting rod on which said intermediate piston slides.

10. A device as claimed in claim 7, wherein said upper piston is provided with a port allowing circulation of the fluid outside said chamber, and said port is provided with a needle valve to shut said port.

11. A device as claimed in claim 7, wherein said intermediate piston is configured to move from the lower piston towards the upper piston of said chamber to transfer fluid out of the chamber.

12. Use of the device as claimed in claim 1, wherein the development of an underground geological site is monitored through fluid sampling in a monitoring well, characterized in that the following stages are carried out:
   a) moving said lower piston so as to bring it into the open position,
   b) lowering the device, with the lower piston in the open position, into the monitoring well,
   c) holding said device with the lower piston in the open position in a predetermined position,
   d) moving said lower piston so as to bring it into the closed position, and
   e) bringing said device back to the surface.

13. Use as claimed in claim 12, wherein the following stages are furthermore carried out after step e):
   f) transferring said fluid out of said chamber of the device, and
   g) performing at least one analysis of the sampled fluid.

14. Use as claimed in claim 12, wherein the development of an underground geological site comprising monitoring a geological $CO_2$ storage site or monitoring a natural gas storage/withdrawal site or monitoring a shale gas development site or monitoring enhanced oil recovery sites using gas injection.

* * * * *